(12) United States Patent
Iwaya

(10) Patent No.: US 7,989,635 B2
(45) Date of Patent: Aug. 2, 2011

(54) METHOD FOR PRODUCING PURIFIED AMMONIUM SALT OF FLUORINATED BIS-SULFONYLIMIDE

(75) Inventor: Masao Iwaya, Tokyo (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 12/699,912

(22) Filed: Feb. 4, 2010

(65) Prior Publication Data

US 2010/0137609 A1 Jun. 3, 2010

Related U.S. Application Data

(63) Continuation of application No. PCT/JP2008/064653, filed on Aug. 15, 2008.

(30) Foreign Application Priority Data

Aug. 17, 2007 (JP) ................................. 2007-212920

(51) Int. Cl.
*C07D 285/01* (2006.01)
*C07D 285/36* (2006.01)
*C07D 285/38* (2006.01)
*C07C 311/01* (2006.01)

(52) U.S. Cl. ............. 548/123; 548/951; 544/5; 564/102

(58) Field of Classification Search .......................... None
See application file for complete search history.

(56) References Cited

U.S. PATENT DOCUMENTS

| 4,387,222 A | 6/1983 | Koshar |
| 2008/0091009 A1 | 4/2008 | Iwaya et al. |
| 2010/0256384 A1 * | 10/2010 | Iwaya ........................... 548/123 |

FOREIGN PATENT DOCUMENTS

| JP | 57-146766 | 9/1982 |
| JP | 9-255685 | 9/1997 |
| JP | 09255685 A * | 9/1997 |
| JP | 2000-86617 | 3/2000 |
| JP | 2000-506132 | 5/2000 |
| JP | 2000-302748 | 10/2000 |
| JP | 2000302748 A * | 10/2000 |
| JP | 2005-89313 | 4/2005 |
| JP | 2005-298375 | 10/2005 |
| WO | 2006-106960 | 10/2006 |
| WO | 2007-072763 | 6/2007 |

OTHER PUBLICATIONS

Juschke, R., et al., Synthesis and structure of potassium 4,4-difluoro-[1,3,2]dithiazetidinide-1,1,3,3-tetraoxide and rubidium 4,4,5,5-tetrafluoro-[1,3,2]dithiazolidine-1,1,3,3-tetraoxide, Zeitschrift fuer Naturforschung, B: Chemical sciences, 1997, 52(3), p. 359-366.
Quek, S. K., et al., Synthesis and properties of N,N'-dialkylimidazolium bis (nonafluorobutane-1-sulfonyl)imides: a new subfamily of ionic liquids, Tetrahedron, 2006, 62(13), p. 3137-3145.

* cited by examiner

*Primary Examiner* — Kamal Saeed
*Assistant Examiner* — Nyeemah A Grazier
(74) *Attorney, Agent, or Firm* — Oblon, Spivak, McClelland, Maier & Neustadt, L.L.P.

(57) ABSTRACT

Methods for preparing an ammonium salt and a lithium salt of a fluorinated bis-sulfonylimide by a practical and efficient method with a high yield with a small number of steps. Further, a high purity ammonium salt of a fluorinated bis-sulfonylimide useful for the method for producing a lithium salt is provided.

A method for producing a purified particulate solid (II) of a salt represented by the formula (1), which comprises suspending a particulate solid (I) of a salt represented by the formula (1) in a solvent comprising an etheric oxygen atom-containing compound, and separating the solvent by filtration:

$$[HNR_3]^+[Q^1\text{-}SO_2\text{-}N\text{-}SO_2\text{-}Q^2]^- \qquad (1)$$

wherein each of R's which may be the same or different, is a hydrogen atom or a $C_{1\text{-}10}$ alkyl group, and each of $Q^1$ and $Q^2$ which are independent of each other, is a monovalent fluoroorganic group, or $Q^1$ and $Q^2$ together form a bivalent fluoroorganic group.

11 Claims, No Drawings

METHOD FOR PRODUCING PURIFIED AMMONIUM SALT OF FLUORINATED BIS-SULFONYLIMIDE

TECHNICAL FIELD

The present invention relates to a method for producing a purified ammonium salt of a fluorinated bis-sulfonylimide, and a method for producing a lithium salt of a fluorinated bis-sulfonylimide.

BACKGROUND ART

An ammonium salt of a fluorinated bis-sulfonylimide such as a compound represented by the formula (1-1) is known as a salt useful as an electrolyte material excellent in electric conductivity and chemical stability:

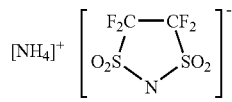  (1-1)

As a general method for purifying an ammonium salt, recrystallization is most widely employed. The present inventors have attempted recrystallization of an ammonium salt represented by the formula (1), however, it is specifically difficult to recrystallize an ammonium salt represented by the above formula (1-1), and they have found that purification by a recrystallization method is difficult:

$$[HNR_3]^+[Q^1\text{-}SO_2\text{—}N\text{—}SO_2\text{-}Q^2]^-  \quad (1)$$

wherein R's which may be the same or different, is a hydrogen atom or a $C_{1-10}$ alkyl group, and each of $Q^1$ and $Q^2$ which are independent of each other, is a monovalent fluoroorganic group, or $Q^1$ and $Q^2$ together form a bivalent fluoroorganic group.

For example, they have attempted a means of suspending the ammonium salt represented by the formula (1) in a poor solvent, and gradually adding a good solvent with heating to dissolve the ammonium salt represented by the formula (1) in the solvent, followed by cooling for recrystallization. However, the ammonium salt solution after addition of the good solvent did not become a uniform solution but was separated into two phases of a good solvent solution phase of the ammonium salt and a poor solvent solution phase, and recrystallization could not be carried out.

Further, the present inventors have attempted, as another recrystallization method, a method of adding a good solvent to the ammonium salt represented by the formula (1), followed by cooling to precipitate crystals. However, although a crystalline substance was formed, the purity of the crystalline substance was low, and the yield was very low, and thus this recrystallization method could not be employed.

Patent Document 1 discloses a purification method of washing $[NH(C_2H_5OCH_3)(C_2H_5)(CH_3)]^+[CF_3\text{—}SO_2\text{—}N\text{—}SO_2\text{—}CF_3]^-$ with an acidic aqueous solution or an alkaline aqueous solution. It is Li, Na, I, Br and the like that can be removed by this method, and even if this method was employed for purification of the ammonium salt represented by the formula (1), the purity was not increased. Further, the decomposition reaction of ammonium represented by the formula (1) occurred.

A lithium salt represented by the formula (3) is a compound which can be used as e.g. an electrolyte for a lithium ion secondary battery. In a case where the lithium salt represented by the formula (3) is used as an electrolyte for a lithium ion secondary battery, high purity of 99 mass % or higher is essential:

$$Li^+[Q^1\text{-}SO_2\text{—}N\text{—}SO_2\text{-}Q^2]^- \quad (3)$$

wherein $Q^1$ and $Q^2$ are as defined for the formula (1).

As a method for purifying a lithium salt, Patent Document 2 discloses a method of reacting $[NH(C_2H_5)_3]^+[CF_3\text{—}SO_2\text{—}N\text{—}SO_2\text{—}CF_3]^-$ with an alkali metal hydroxide such as sodium hydroxide to convert it to an alkali metal salt, followed by crystallization.

However, it is a sodium salt that is formed in a case where sodium hydroxide is used, and salt exchange is required to obtain a lithium salt. A method of using lithium hydroxide instead of sodium hydroxide may be mentioned so as to directly obtain a lithium salt, but a solvent is coordinated to the precipitated lithium salt, and a complicated step to remove the solvent is required. Further, if impurities to be removed are reacted with an alkali metal hydroxide, an alkali metal salt of impurities will be formed, and its removal is more difficult.

Patent Document 3 discloses as a method for purifying $Li^+[CF_3\text{—}SO_2\text{—}N\text{—}SO_2\text{—}CF_3]^-$, a method of recrystallizing it from 1,4-dioxane, dissolving it in a polar solvent having a boiling point of at most 100° C., followed by filtration, and removing the solvent. The present inventors have practically conducted this method, and they have found problems in this method such that the yield was so low as 60%, removal of the solvent was very difficult, and removal of the solvent took a long period of time.

Patent Document 1: JP-A-2005-298375
Patent Document 2: JP-A-2000-302748
Patent Document 3: JP-A-9-255685

DISCLOSURE OF THE INVENTION

Object to be Accomplished by the Invention

The object of the present invention is to provide a method for producing a high purity ammonium salt of a fluorinated bis-sulfonylimide simply and efficiently, and a method for producing a high purity lithium salt of a fluorinated bis-sulfonylimide using the purified ammonium salt as a starting material.

That is, methods for producing an ammonium salt and a lithium salt of a fluorinated bis-sulfonylimide using a practical and efficient method with a high yield with a small number of steps, are provided. Further, the present invention provides a high purity ammonium salt of a fluorinated bis-sulfonylimide useful for the above method for producing a lithium salt.

Means to Accomplish the Object

The present invention provides the following.

[1] A method for producing a purified particulate solid (II) of a salt represented by the following formula (1), which comprises suspending a particulate solid (I) of a salt represented by the following formula (1) in a solvent comprising an etheric oxygen atom-containing compound, and separating the solvent by filtration:

$$[HNR_3]^+[Q^1\text{-}SO_2\text{—}N\text{—}SO_2\text{-}Q^2]^- \quad (1)$$

wherein each of R's which may be the same or different, is a hydrogen atom or a $C_{1-10}$ alkyl group, and each of $Q^1$ and $Q^2$ which are independent of each other, is a monovalent fluoroorganic group, or $Q^1$ and $Q^2$ together form a bivalent fluoroorganic group.

[2] The method according to the above [1], wherein the purity of the particulate solid (I) as measured by NMR is 80 mol % or higher and less than 99 mol %, and the purity of the particulate solid (II) as measured by NMR is 99 mol % or higher.

[3] The method according to the above [1] or [2], wherein the particulate solid (I) of a salt represented by the formula (1) is suspended in the solvent comprising an etheric oxygen atom-containing compound by heating with stirring and swelled, and then filtration is carried out.

[4] The method according to any one of the above [1] to [3], wherein the solvent comprising an etheric oxygen atom-containing compound is used in an amount of from 0.5 to 20 times the mass of the particulate solid (I).

[5] The method according to any one of the above [1] to [4], wherein the solvent comprising an etheric oxygen atom-containing compound is a cyclic ether compound.

[6] The method according to any one of the above [1] to [5], wherein the solvent comprising an etheric oxygen atom-containing compound is 1,4-dioxane.

[7] The method according to any one of the above [1] to [6], wherein the salt represented by the formula (1) is a salt represented by the following formula (1-1):

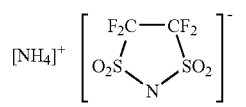   (1-1)

[8] An ammonium salt represented by the following formula (1), which has a purity as measured by NMR of 99 mol % or higher:

   (1)

wherein each of R's which may be the same or different, is a hydrogen atom or a $C_{1-10}$ alkyl group, and each of $Q^1$ and $Q^2$ which are independent of each other, is a monovalent fluoroorganic group, or $Q^1$ and $Q^2$ together form a bivalent fluoroorganic group.

[9] An ammonium salt represented by the following formula (1-1), which has a purity as measured by NMR of 99 mol % or higher:

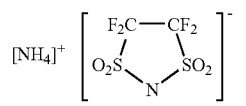   (1-1)

[10] A method for producing a lithium salt represented by the following formula (3), which comprises obtaining a particulate solid (II) of a salt represented by the formula (1) by the method as defined in any one of the above [1] to [7], reacting the particulate solid (II) with concentrated sulfuric acid to obtain an imidic acid represented by the following formula (2), and reacting the imidic acid with a compound containing a lithium ion to obtain a lithium salt represented by the following formula (3):

$$Q^1\text{-}SO_2\text{—}NH\text{—}SO_2\text{-}Q^2 \quad (2)$$

$$Li^+[Q^1\text{-}SO_2\text{—}N\text{—}SO_2\text{-}Q^2]^- \quad (3)$$

wherein each of R's which may be the same or different, is a hydrogen atom or a $C_{1-10}$ alkyl group, and each of $Q^1$ and $Q^2$ which are independent of each other, is a monovalent fluoroorganic group, or $Q^1$ and $Q^2$ together form a bivalent fluoroorganic group.

[11] A method for producing a lithium salt represented by the following formula (3), which comprises obtaining a particulate solid (II) of a salt represented by the formula (1) by the method as defined in the above [1], and reacting the particulate solid (II) with a compound containing a lithium ion to obtain a lithium salt represented by the following formula (3):

$$Q^1\text{-}SO_2\text{—}NH\text{—}SO_2\text{-}Q^2 \quad (2)$$

$$Li^+[Q^1\text{-}SO_2\text{—}N\text{—}SO_2\text{-}Q^2]^- \quad (3)$$

wherein each of R's which may be the same or different, is a hydrogen atom or a $C_{1-10}$ alkyl group, and each of $Q^1$ and $Q^2$ which are independent of each other, is a monovalent fluoroorganic group, or $Q^1$ and $Q^2$ together form a bivalent fluoroorganic group.

[12] The method according to the above [10] or [11], wherein the purity of the lithium salt represented by the formula (3) as measured by NMR is 99 mol % or higher.

[13] The method according to any one of the above [10] to [12], wherein the compound containing a lithium ion is lithium hydroxide, lithium carbonate or lithium hydrogencarbonate.

[14] The method according to any one of the above [10] to [13], wherein the lithium salt represented by the formula (3) is a lithium salt to be used as an electrolyte for a lithium ion secondary battery.

Effects of the Invention

According to the present invention, a high purity ammonium salt of a fluorinated bis-sulfonylimide can be obtained by a practical and efficient method with a high yield with a small number of steps. Further, according to the present invention, a high purity lithium salt of a fluorinated bis-sulfonylimide can be obtained simply and efficiently. Further, according to the present invention, a high purity lithium salt of a fluorinated bis-sulfonylimide useful for the method for producing the lithium salt can be provided.

BEST MODE FOR CARRYING OUT THE INVENTION

In the present specification, groups are as defined above unless otherwise specified. In the present specification, a salt represented by the formula (1) will be referred to as a salt (1), and an anion represented by the formula (A) will be referred to as an anion (A). The same applies to salts, anions, cations, compounds and the like represented by other formulae.

The salt (1) in the present invention is a salt made of the following cation (C) and anion (A):

$$[HNR_3]^+ \quad (C)$$

$$[Q^1\text{-}SO_2\text{—}N\text{—}SO_2\text{-}Q^2]^- \quad (A)$$

$$[HNR_3]^+[Q^1\text{-}SO_2\text{—}N\text{—}SO_2\text{-}Q^2]^- \quad (1)$$

In the cation (C), in a case where R is a $C_{1-10}$ alkyl group, R is preferably a methyl group, an ethyl group, a n-propyl group, an isopropyl group or a n-butyl group.

The cation (C) may, for example, be ammonium, trimethylammonium, triethylammonium, tri-n-propylammonium, tri-isopropylammonium, tri-n-butylammonium, dimethylethylammonium, methyldiethylammonium, dimethyl-n-propylammonium, methyl-di-n-propylammonium, dimethylisopropylammonium, methyldiisopropylammonium, dimethyl-n-butylammonium, methyl-di-n-butylammonium, diethyl-n-propylammonium, ethyl-di-n-propylammonium, diethylisopropylammonium, ethyldiisopropylammonium, diethyl-n-butylammonium or ethyl-di-n-butylammonium.

In a case where the cation (C) is ammonium ($NH_4^+$) or triethylammonium, preparation of an ammonium salt is easy, such being preferred.

In the anion (A), in a case where each of $Q^1$ and $Q^2$ is a monovalent fluoroorganic group, it is preferably a monovalent fluorinated hydrocarbon group, more preferably a fluorinated alkyl group, a fluorinated alkenyl group or a fluorinated allyl group, particularly preferably a perfluoroalkyl group, a perfluoroalkenyl group or a perfluoroallyl group. Each of the fluorinated alkyl group and the fluorinated alkenyl group may have a linear structure or a branched structure.

In a case where $Q^1$ and $Q^2$ together form a bivalent fluoroorganic group, it is preferably a fluorinated alkylene group, particularly preferably a perfluoroalkylene group.

It is preferred that $Q^1$ and $Q^2$ are a perfluoroalkyl group having 1 or 2 carbon atoms, or they together form a $C_{1-3}$ perfluoroalkylene group.

Specifically, the anion (A) is preferably any one of anions represented by the following formulae:

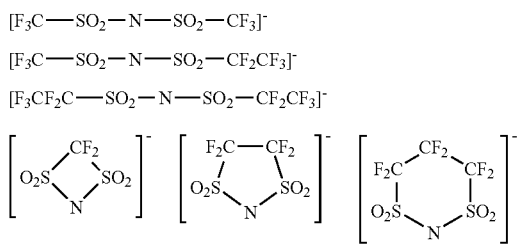

In the present invention, the salt (1) is particularly preferably the following ammonium salt (1-1):

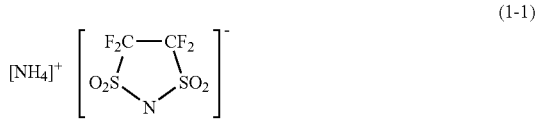

(1-1)

As a means of obtaining the salt (1), for example, a method disclosed in WO 2006/106960 (Example 4), a method disclosed in JP-A-08-081436, or a method disclosed in WO97/23448 may be mentioned.

The particulate solid (I) of the salt (1) in the present invention is obtained by concentrating a reaction solvent solution containing a salt (I) formed by the production method as disclosed in such a document. In a case where a solid is contained in the reaction solvent solution before the concentration, it is preferred to preliminarily remove the solid by a method such as filtration, whereby the purification method will efficiently be carried out.

A compound contained in the particulate solid (I) and to be removed by the purification method of the present invention may, for example, be a neutral organic substance which is not charged and which is a solid at room temperature. For example, impurities in a case of production by the production method disclosed in the above document may, for example, be $HN_2SO_2CF_2CF_2SO_2NH_2$ and $FO_2SCF_2CF_2SO_2NH_2$.

The purity of the particulate solid (I) used for the production method of the present invention is preferably 80 mol % or higher, particularly preferably from 85 to 99 mol %, especially preferably from 95 to 99 mol %.

The value of the purity in the present invention is a value quantified by an NMR (nuclear magnetic resonance) method unless otherwise specified. A nuclear species in the NMR method may, for example, be $^1H$, $^{19}F$ or $^{13}C$, and is preferably $^{19}F$.

The particle size of the particulate solid (I) is preferably at most a particle size to such an extent that the particles are suspended and at least a particle size to such an extent that when the particles are suspended in a solvent, not all the particles are dissolved. Usually, the maximum particle size of the particles is preferably from 0.1 mm to 3.0 mm, more preferably from 0.1 mm to 1.0 mm. The particle size may be measured by a method such as classification. Further, the particulate solid (I) may be in a crystalline state, in an amorphous state or in a mixed state thereof.

In the production method of the present invention, first, the particulate solid (I) of the salt (1) is suspended in a solvent comprising an etheric oxygen atom-containing compound.

The solvent comprising an etheric oxygen atom-containing compound (hereinafter referred to as an ether solvent) may be a cyclic ether compound such as 1,4-dioxane, 1,3-dioxane, 1,3-dioxolane, tetrahydrofuran or tetrahydropyran; or an acyclic ether compound such as diethyl ether, methyl-t-butyl ether, diethylene glycol dimethyl ether, diethylene glycol diethyl ether, diethylene glycol dibutyl ether, tetraethylene glycol dimethyl ether, tetraethylene glycol diethyl ether or tetraethylene glycol dibutyl ether, and it is preferably a cyclic ether compound, particularly preferably 1,4-dioxane, whereby the solubility of the salt (1) is low, the solubility of impurities is high, and accordingly efficient purification is possible.

In the present specification, "being suspended" means a state where in a solution having a part of the salt (1) dissolved in a solvent, the rest of the particulate solid (1) is dispersed. Under normal conditions, a solution having the salt (1) dissolved can be a saturated solution of the salt (1). The amount of the ether solvent is preferably from 0.5 to 20 times, particularly preferably from 1 to 5 times the mass of the particulate solid (I) to be purified. When the amount of the solvent is within such a range, the particulate solid (I) will be sufficiently suspended, and the yield will be high.

The temperature at the suspending operation may be the boiling point of the solvent or lower, and is preferably within a range of from 10 to 80° C. in view of easy operation and simple apparatus structure, particularly preferably from 20 to 60° C. Further, after the suspending operation, the suspension is preferably stirred.

The time for the suspending operation is preferably at least 10 minutes, particularly preferably from 10 minutes to 4 hours, especially preferably from 30 minutes to 2 hours, after the particulate solid (I) is suspended in the ether solvent and swelling of the particulate solid (I) is confirmed.

In the present invention, the particulate solid (I) is suspended, and then the ether solvent is separated by filtration to obtain a purified particulate solid (II). As the filtration method, any method such as centrifugal separation, pressurized filtration, vacuum filtration or normal pressure filtration may be selected. The particulate solid (II) obtained by filtration may be in a crystalline state, in an amorphous state or in a mixed state thereof.

The obtained particulate solid (II) is preferably washed with a washing solvent from the viewpoint of improvement in the purity. The washing solvent is preferably an ether solvent which is the same as or different from the ether solvent used for the suspending operation, or a solvent other than an ether solvent may be used. The washing solvent is preferably a nonpolar solvent from the viewpoint of the recovery rate of the particulate solid (II). The washing solvent may, for example, be a cyclic ether compound such as 1,4-dioxane, 1,3-dioxane, 1,3-dioxolane, tetrahydrofuran or tetrahydropyran; an acyclic ether compound such as diethyl ether, methyl-t-butyl ether, diethylene glycol dimethyl ether, diethylene glycol diethyl ether, diethylene glycol dibutyl ether, tetraethylene glycol dimethyl ether, tetraethylene glycol diethyl ether or tetraethylene glycol dibutyl ether; n-hexane, n-pentane, n-heptane, n-octane, benzene, toluene, xylene, cyclohexane, dichloromethane, chloroform, pentafluorodichloropropane or 1H-perfluorohexane.

The particulate solid (II) obtained by filtration is then preferably dried. The drying method is not particularly limited, and a depressurizing method with heating, or a method of making a dry inert gas flow with heating, is usually employed. In the case of heating, the temperature is not particularly limited, and it is preferably the boiling point of the solvent or higher, and is preferably at most a temperature which is higher by 50° C. than the boiling point of the solvent, with a view to suppressing decomposition of an aimed product e.g. by local overheating. Further, the inert gas may, for example, be a rare gas, nitrogen gas or carbon dioxide gas, and is preferably nitrogen gas from the viewpoint of availability and handling efficiency.

According to the production method of the present invention, a purified salt (1) can be obtained as the particulate solid (II). The purity of the purified salt (1) is preferably 90 mol % or higher, particularly preferably from 98 to 100 mol %, especially preferably from 99 to 100 mol %. Such a high purity salt (1) is a novel salt which could not be obtained before.

The application of the high purity salt (1) obtained by the production method of the present invention is not particularly limited, and it may be used, for example, as a material of a lithium salt (3) as an electrolyte for a lithium ion secondary battery.

A method for producing a lithium salt (3) using the salt (1) obtained by the production method of the present invention is shown below.

eau, Inorganic Chemistry, Vol. 23, No. 23, 1984, p. 3720, and a method disclosed in JP-A-57-146776 (Example 1) may be mentioned.

Specifically, a method of mixing the compound (1) with concentrated sulfuric acid, followed by heating under reduced pressure conditions so that the compound (2) distills by distillation, or a method of making an aqueous solution of the compound (1) pass through an acid type cation exchange resin such as sulfonated polystyrene to obtain a compound (2) may, for example, be mentioned. The former method is particularly preferred, since metal impurities, etc. can be removed in the distillation step.

As a method of obtaining the lithium salt (3) from the imidic acid (2), a method disclosed in JP-A-2003-192661 (Examples 8 to 14) may be mentioned. The compound containing a lithium ion to be reacted with the imidic acid (2) is preferably lithium hydroxide, lithium carbonate or lithium hydrogencarbonate, more preferably lithium hydroxide. Such a lithium compound is preferably used since it is readily available and has high reactivity, and the by-product is carbon dioxide gas or water and can easily be separated.

In the above method of obtaining the lithium salt (3) from the imidic acid (2), a solvent may be used. As the solvent, a non-aqueous solvent may be used, or water may be used. The non-aqueous solvent is preferably a solvent which is not decomposed by an acid since the compound (2) is very strongly acidic, and a non-aqueous solvent such as methanol or ethanol is particularly preferred.

As the method of obtaining the lithium salt (3) in the method 2, for example, a method of adding lithium hydroxide monohydrate to the salt (1) dissolved in tetrahydrofuran, followed by boiling until generation of ammonia gas is no more observed for reaction, as disclosed in JP-A-2000-506132 (Example 2) may be mentioned. As the solvent, an optional solvent may be used, but it is required to select a solvent which is not decomposed by ammonia. Further, in a case where the end point of the reaction is to be detected by ammonia gas generation, a solvent other than a solvent in which ammonia is well dissolved, such as water, is preferably used.

In the method 1 and the method 2, in a case where a high purity reaction reagent is used, a high purity lithium salt (3) is obtained. A lithium salt (3) having a purity of 99 mol % or

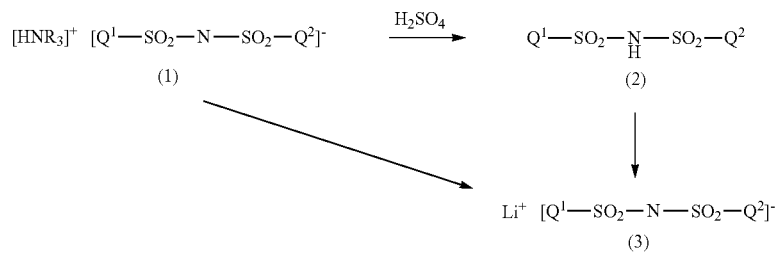

For example, (method 1): a method for producing a lithium salt (3) by reacting a purified salt (1) with concentrated sulfuric acid to obtain an imidic acid (2), and reacting the imidic acid with a compound having a lithium ion, or (method 2): a method of reacting the purified salt (1) with a compound having a lithium ion to produce a lithium salt (3).

As a method of obtaining the imidic acid (2) in the method (1), for example, a method disclosed in "Synthesis, properties, and reactions of bis((trifluoromethyl)sulfonyl)imide, $(CF_3SO_2)_2NH$" by Jerry Foropoulos Jr., Darryl D. DesMarthigher is obtained, and usually a lithium salt (3) having a purity of 99.5 mol % or higher is obtained, for example, by using sulfuric acid having a purity of at least 98 vol % as concentrated sulfuric acid, using a compound containing a lithium ion having a purity of at least 99 mass %, using a solvent having a purity of at least 99 mass %, and using other reaction reagent having a purity of at least 99 mass % if used.

In a case where a high purity lithium salt (3) is obtained by the method 1 or the method 2, usually no purification step is required, and a lithium salt (3) having an aimed purity can be obtained only by post-treatment such as removal of the solvent. The lithium salt (3) may be in a crystalline state, in an amorphous state or in a mixed state thereof.

The purity of the lithium salt (3) is preferably 99 mol % or higher, particularly preferably 99.5 mol % or higher, especially preferably 99.9 mol % or higher. Particularly when the lithium salt (3) is obtained by the method 1, since the distillation step is a step capable of removing metal impurities, a lithium salt (3) having an extremely low metal content can be obtained.

The obtained high purity lithium salt (3) can be a useful lithium salt capable of having a potential window broader than from 0 to 4.2 V as an electric potential versus lithium.

The high purity ammonium salt of a fluorinated bis-sulfonylimide obtained by the present invention may be used as e.g. an intermediate for preparation of an ionic liquid, an electric conductivity-imparting agent, a flame retardancy-imparting agent. Further, the high purity lithium salt (3) of the imide is useful as e.g. an electrolyte, an intermediate for preparation of an ionic liquid, an electric conductivity-imparting agent or a flame retardancy-imparting agent.

EXAMPLES

Now, the present invention will be described in further detail with reference to Examples, but the present invention is by no means restricted thereto.

In measurement of the purity by $^{19}$F-NMR, a peak of $CF_2$ in the $SO_2$—$CF_2$—$CF_2$—$SO_2$ structure and peaks other than the peak of $CF_2$ were measured, and the structure of impurities based on the peaks other than $CF_2$ was identified for quantitative determination. In the following description, the purity and the yield are based on mol % unless otherwise specified.

Example 1

Example of the Present Invention

Example for Preparation of Compound (1-1)

A particulate solid of the following ammonium salt (1-1) was prepared in the same manner as in the method disclosed in Example 4 of WO2006/106960. The purity of the ammonium salt (1-1) before purification as measured by $^{19}$F-NMR was 98.5%.

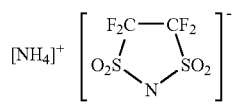

(1-1)

Example for Preparation of Ammonium Salt (1-1)

The particulate solid (380.0 g) of the ammonium salt (1-1) having an NMR purity of 98.5% was suspended in 1,4-dioxane (760.0 g) and stirred at 40° C. for 4 hours while it was swelled. 4 Hours later, dioxane was separated by filtration, and the obtained particulate solid was washed with 1,4-dioxane (380.0 g) twice, and then the solvent was removed by vacuum drying. 374.2 g of a particulate solid of ammonium salt (1-1) was obtained, and the yield was 99.9%. The purity was measured by $^{19}$F-NMR, whereupon it was improved to 99.9%.

Example 2

Example of the Present Invention

Example for Preparation of Imidic Acid (2-1)

The ammonium salt (1-1) (300 g) before purification obtained in Example 1 and concentrated sulfuric acid (600 g) having a purity of 98 vol % or higher were charged into a 2 L three-necked flask. This three-necked flask and a 2 L receiver were connected by a glass tube. The glass tube was kept at 60° C. or higher by a ribbon heater to prevent coagulation of the imidic acid (2-1). The 2 L receiver was cooled with ice and connected with a vacuum pump so that the whole system was a recovery system for the imidic acid. The pressure in the system was reduced to 266 Pa (absolute pressure), and the three-necked flask was heated in an oil bath. Distillation started when the internal temperature of the three-necked flask exceeded 80° C., and the following imidic acid (2-1) was solidified and recovered in the receiver cooled with ice. The reaction was completed after the temperature raising was continued until the internal temperature reached 100° C. and as a result, 272.2 g of the imidic acid (2-1) in the form of a white solid was obtained in the receiver. The yield was 97.1%. The purity was measured by $^{19}$F-NMR, whereupon it was 99.9%.

(2-1)

Example for Preparation of Lithium Salt (3-1)

To the obtained imidic acid (2-1) (272.2 g), deionized water (500 mL) was charged to obtain an aqueous solution. A lithium hydroxide aqueous solution (concentration: 10 mass %) was dropwise added with stirring while the pH of the aqueous solution was monitored, and dropwise addition was continued until the pH exceeded 7. After completion of dropwise addition of the lithium hydroxide aqueous solution, stirring was continued for one hour. Then, water was distilled off, followed by vacuum drying at 100° C. 276.0 g of lithium salt (3-1) in the form of a white solid was obtained, and the yield was 99.0%. The purity was measured by $^{19}$F-NMR, whereupon it was 99.9%.

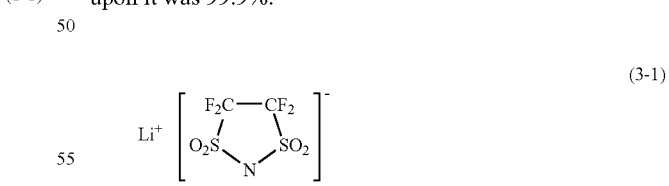

(3-1)

Example 3

Reference Example

The ammonium salt (1-1) (100 g) before purification obtained in Example 1 was used without purification by 1,4-dioxane to prepare the imidic acid (2-1) in the same manner as in Example 2. 90.6 g of imidic acid (2-1) was obtained, but the imidic acid (2-1) was slightly brown. The yield was 96.4%.

To the imidic acid (2-1) (90.6 g), deionized water (300 mL) was charged to prepare lithium salt (3-1) in the same manner as in Example 2. 91.8 g of particles of lithium salt (3-1) in the form of a solid were obtained, but the particles were slightly yellow. The yield was 98.9%. The purity was measured by $^{19}$F-NMR, whereupon it was 98.0%.

Example 4

Reference Example

The lithium salt (3-1) (91.8 g) obtained in Example 3 was suspended in 1,4-dioxane (100 mL), and acetonitrile was gradually added while the internal temperature was kept at 60° C. to obtain a uniform solution. This solution was cooled overnight in a refrigerator kept at 3° C., whereupon a white crystalline substance was precipitated. Then, the substance was recovered by filtration. The recovered substance was vacuum dried at from 80 to 120° C. for 100 hours. 57.8 g of a white crystalline substance was obtained, and it was confirmed that 5 mass % of 1,4-dioxane remained. The purity of the compound other than the solvent was measured, whereupon it was 99.9%.

The amount of remaining 1,4-dioxane and the amount of the lithium salt were quantitatively determined by measuring $^{19}$F-NMR and $^1$H-NMR using $CF_3CH_2OH$ as an internal standard substance.

Then, to remove remaining 1,4-dioxane, a step of dissolving the substance in n-butylonitrile (100 mL) and distilling off the solvent was repeatedly carried out 4 times. The substance was vacuum dried at 100° C. for 12 hours to recover 57.5 g of lithium salt (3-1). The yield was 63.8%. By $^1$H-NMR, no 1,4-dioxane remained, and the purity as measured by $^{19}$F-NMR was 99.9%. It is considered that removal of the solvent from the lithium salt is difficult since coordination properties of 1,4-dioxane to lithium ions is strong.

Example 5

Reference Example

The ammonium salt (1-1) (5.0 g) before purification obtained in Example 1 was dispersed in methyl-t-butyl ether (5 mL) and gradually heated, whereupon a uniform solution was obtained at 50° C. The solution was cooled to −78° C., whereupon a small amount of a precipitate was obtained. The precipitate was subjected to filtration and dried, and the purity was measured by $^{19}$F-NMR and as a result, the purity was 98.0%, and high purity could not be achieved.

Example 6

Reference Example

The ammoniums salt (1-1) (5.0 g) before purification obtained in Example 1 was dispersed in chloroform (5 mL), 25 drops of acetonitrile were added, and the dispersion was gradually heated, whereupon a uniform solution was obtained at 50° C. The solution was gradually cooled to room temperature, whereupon it was separated into two phases of an acetonitrile phase in which the ammonium salt (1-1) was dissolved and a chloroform phase. The acetonitrile phase containing the ammonium salt (1-1) as an upper phase was analyzed by $^{19}$F-NMR and as a result, the purity excluding the solvent was 98.0%, and no high purity could be achieved.

Example 7

Reference Example

Purification was attempted with reference to a method disclosed in JP-A-2005-298375. That is, the ammonium salt (1-1) (5.0 g) before purification obtained in Example 1 was dissolved in methyl-t-butyl ether (10 mL), stirred in an aqueous solution having lithium hydroxide (1.42 g) dissolved in deionized water (10 mL), and reacted at 50° C. for 3 hours. Then, the aqueous phase as a lower phase was separated, concentrated and vacuum dried with heating at 100° C. to obtain lithium salt (3-1) having a $^{19}$F-NMR purity of 99.0%. The lithium salt (3-1) was dissolved in a solvent mixture of ethylene carbonate and ethyl methyl carbonate in a volume ratio of 1:1 at a concentration of 1 mol/L to prepare a solution, and the oxidation potential was measured by a cell using platinum for a counter electrode and a working electrode and lithium metal for a difference electrode. As a result, oxidation peak which was not derived from the compound (3-1) was observed at about 3.5 V. That is, the obtained lithium salt (3-1) has insufficient oxidation resistance for an application such as a lithium battery material.

INDUSTRIAL APPLICABILITY

According to the production method of the present invention, a high purity ammonium salt of a fluorinated bis-sulfonylimide can be prepared simply and efficiently without use of a special apparatus nor reagent, and accordingly it is an industrially useful method.

Further, an ammonium salt of a fluorinated bis-sulfonylimide obtained by the production method of the present invention is useful as e.g. an intermediate for preparation of an ionic liquid, an electric conductivity-imparting agent or a flame retardancy-imparting agent, and further, the lithium salt of the imide is useful as e.g. an electrolyte, an intermediate for preparation of an ionic liquid, an electric conductivity-imparting agent or a flame retardancy-imparting agent.

The entire disclosure of Japanese Patent Application No. 2007-212920 filed on Aug. 17, 2007 including specification, claims and summary is incorporated herein by reference in its entirety.

What is claimed is:

1. A method for producing a purified particulate solid (II) of a salt represented by formula (1), which comprises:
   suspending a particulate solid (I) of a salt in a solvent comprising an etheric oxygen atom-containing compound,
   separating the solvent by filtration,
   and recovering particulate solid (II) of said salt;
   wherein particulate solids (I) and (II) of a salt are represented by the formula:

$$[HNR_3]^+[Q^1\text{-}SO_2\text{—}N\text{—}SO_2\text{—}Q^2]^- \qquad (1)$$

wherein each of R's which may be the same or different, is a hydrogen atom or a $C_{1\text{-}10}$ alkyl group, and each of $Q^1$ and $Q^2$ which are independent of each other, is a monovalent fluoroalkyl group, or $Q^1$ and $Q^2$ together form a bivalent fluoroorganic group which are 4, 5 or 6-membered rings;
   wherein particulate solid (I) has a purity ranging from 80 mol. % to 99 mol. % as measured by NMR (nuclear magnetic resonance); and
   wherein particular solid (II) has a purity of 90 mol. % or higher as measured by NMR (nuclear magnetic resonance), and wherein the purity of particular solid (II) is higher than the purity of particular solid (I).

2. The method according to claim 1, wherein the purity of the particulate solid (I) as measured by NMR is 80 mol % or higher and less than 99 mol %, and the purity of the particulate solid (II) as measured by NMR is 99 mol % or higher.

3. The method according to claim 1, wherein the particulate solid (I) of a salt represented by the formula (1) is suspended in the solvent comprising an etheric oxygen atom-containing compound by heating with stirring and swelled, and then separated from the solvent by filtration, thus providing particulate solid (II) of said salt.

4. The method according to claim 1, wherein the solvent comprising an etheric oxygen atom-containing compound is used in an amount of from 0.5 to 20 times the mass of the particulate solid (I).

5. The method according to claim 1, wherein the solvent comprising an etheric oxygen atom-containing compound is a cyclic ether compound.

6. The method according to claim 1, wherein the solvent comprising an etheric oxygen atom-containing compound is 1,4-dioxane.

7. The method according to claim 1, wherein the salt represented by the formula (1) is a salt represented by the following formula (1-1):

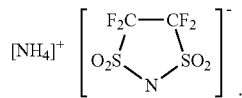

(1-1)

8. A method for producing a purified particulate solid (II) of a salt represented by formula (1), which comprises:
  suspending a particulate solid (I) of a salt in a solvent comprising an etheric oxygen atom-containing compound,
  separating the solvent by filtration,
  and recovering particulate solid (II) of said salt;
  wherein particulate solids (I) and (II) of a salt are represented by the formula:

$$[HNR_3]^+[Q^1\text{-}SO_2\text{—}N\text{—}SO_2\text{-}Q^2]^- \quad (1)$$

wherein
  each of R's which may be the same or different, is a hydrogen atom or a $C_{1\text{-}10}$ alkyl group, and
  $Q^1$ and $Q^2$ each independently represent a fluoralkyl group or $Q^1$ and $Q^2$ together form a bivalent fluoroethyl group whereby a five-membered ring is formed;
  wherein particulate solid (I) has a purity ranging from 80 mol. % to 99 mol. % as measured by NMR (nuclear magnetic resonance); and
  wherein particulate solid (II) has a purity of 90 mol. % or higher as measured by NMR (nuclear magnetic resonance), and
  wherein the purity of particular solid (II) is higher than the purity of particular solid (I).

9. The method of claim 8, wherein $Q^1$ and $Q^2$ each independently represent a fluoralkyl group.

10. The method of claim 8, wherein $Q^1$ and $Q^2$ together form a bivalent fluoroethyl group whereby a five-membered ring is formed.

11. The method of claim 8, wherein particulate solids (I) and (II) of a salt comprise a cation that is $[HNR_3]^+$ where at least one of the three R groups is $C_1$-$C_{10}$ alkyl and the anion is:

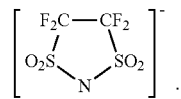

(1-1)

* * * * *